United States Patent
Botti et al.

(10) Patent No.: US 7,566,697 B2
(45) Date of Patent: Jul. 28, 2009

(54) CARBOXY PROTECTION STRATEGIES FOR ACIDIC C-TERMINAL AMINO ACIDS IN CHEMICAL LIGATION OF OLIGOPEPTIDES

(75) Inventors: Paolo Botti, Vessy (CH); Matteo Villain, Rancho Palos Verde, CA (US); Sonia Manganiello, Geneva (CH); Hubert Gaertner, Archamps (FR)

(73) Assignee: Amylin Pharmaceuticals, Inc., San Diego, CA (US)

( * ) Notice: Subject to any disclaimer, the term of this patent is extended or adjusted under 35 U.S.C. 154(b) by 559 days.

(21) Appl. No.: 10/517,392

(22) PCT Filed: Jun. 9, 2003

(86) PCT No.: PCT/IB03/05473

§ 371 (c)(1),
(2), (4) Date: Jun. 17, 2005

(87) PCT Pub. No.: WO2004/007661

PCT Pub. Date: Jan. 22, 2004

(65) Prior Publication Data

US 2005/0261473 A1    Nov. 24, 2005

Related U.S. Application Data

(60) Provisional application No. 60/387,825, filed on Jun. 10, 2002.

(51) Int. Cl.
*A61K 38/08* (2006.01)
(52) U.S. Cl. .................. 514/15; 530/300; 530/327; 530/338; 530/334
(58) Field of Classification Search .............. None
See application file for complete search history.

(56) References Cited

U.S. PATENT DOCUMENTS 6,184,344 B1    2/2001    Kent et al.

OTHER PUBLICATIONS

Hackeng, 1999, PNAS, 96, 10068-10073.*
Botti, et al., 2001, Tetrahedron Letters, 42, 1831-1833.*
Dawson, et al., 1997, JACS, 119, 4325-4329.*
al-Obeidi, F., et al., Int J Pept Protein Res 1990; 35(3):215-8.
Blake, Int J Peptide Protein Res, 17:273(1981).
Bodansky, M., et al. J Org Chem 1978; 43: 3071-3073.
Botti, Paolo, Tetrahedron Letters, 42: 1831-1833 (2001).
Canne, et al., J Am Chem Soc, 121: 8720-8727 (1999).
Canne, et al., Tetrahedron Letters, 36: 1217-1220 (1995).
Dawson, et al., Science, 266: 776-779 (1994).
Hackeng, et al., Proc Natl Acad Sci, 94: 7845-7850 (1997).
Hackeng, et al., Proc Natl Acad Sci, 96: 10068-10073 (1999).
Ingenito, et al., J Am Chem Soc, 121: 11369-11374 (1999).
Lee, Y.S., et al., J Pept Res, 54(4): 328-35 (1999).
Low, et al., Proc Natl Acad Sci, 98: 6554-6559 (2001).
Robles, J. et al., Int J Peptide Protein Res, 43(4): 359-62 (1994).
Schnolzer, et al., Int J Peptide Protein Res 40:, 180-193.
Woodward, R.B., et al., J Am Chem Soc, 88: 852 (1966).
Xue, C.B., et al., Int J Pept Protein Res, 37(6): 476-86 (1991).

* cited by examiner

*Primary Examiner*—Andrew D Kosar
*Assistant Examiner*—Satyanarayana Gudibande

(57) ABSTRACT

The present invention provides methods of assembling oligopeptides or polypeptides in a native chemical ligation reaction that eliminates the formation of unwanted side products resulting from the presence of an unprotected acidic C-terminal oligopeptide thioester. An important aspect of the present invention is providing side chain protected acidic C-terminal oligopeptide thioesters. The present invention is useful in methods for chemical synthesis of oligopeptides, polypeptides and proteins and improves the efficiency of native chemical ligation reactions, particularly where aspartyl or glutamyl peptide fragments are used to assemble an oligopeptide, polypeptide or protein product.

6 Claims, 6 Drawing Sheets

SCHEME 1

SCHEME 2

SCHEME 3

SEQUENCE LISTING

<160> NUMBER OF SEQ ID NOS: 21

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Lys Leu Leu Met
  1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Leu-Pam

<400> SEQUENCE: 2

Tyr Ala Lys Tyr Ala Lys Leu
  1               5

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp(Mop)

<400> SEQUENCE: 3

Leu Tyr Arg Ala Asp Cys Ser Tyr Arg Phe Leu
  1               5                  10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp-thioester

<400> SEQUENCE: 4

Leu Tyr Arg Ala Asp
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (5)
<223> OTHER INFORMATION: Glu-thioester

<400> SEQUENCE: 5

Leu Tyr Arg Ala Glu
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ser Tyr Arg Phe Leu
 1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Tyr Arg Ala Asp Cys Ser Tyr Arg Phe Leu
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Tyr Arg Ala Glu Cys Ser Tyr Arg Phe Leu
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp(beta)

<400> SEQUENCE: 9

Leu Tyr Arg Ala Asp Cys Ser Tyr Arg Phe Leu
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)
<223> OTHER INFORMATION: Glu(gamma)

<400> SEQUENCE: 10

Leu Tyr Arg Ala Glu Cys Ser Tyr Arg Phe Leu
 1               5                  10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Glu(OFm)-thioester

<400> SEQUENCE: 11

Leu Tyr Arg Ala Glu
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Glu(OPse)-thioester

<400> SEQUENCE: 12

Leu Tyr Arg Ala Glu
 1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Glu(OPse)

<400> SEQUENCE: 13

Leu Tyr Arg Ala Glu Cys Ser Tyr Arg Phe Leu
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Glu(OFm)

<400> SEQUENCE: 14
```

```
Leu Tyr Arg Ala Glu Cys Ser Tyr Arg Phe Leu
 1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Fmoc-Asp(Troc)

<400> SEQUENCE: 15

Asp Tyr Ala Lys Tyr Ala Lys Leu
 1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Asp(OPac)

<400> SEQUENCE: 16

Asp Tyr Ala Lys Tyr Ala Lys Leu
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Asp(OMop)

<400> SEQUENCE: 17

Asp Tyr Ala Lys Tyr Ala Lys Leu
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Asp(diMeOPac)

<400> SEQUENCE: 18

Asp Tyr Ala Lys Tyr Ala Lys Leu
 1               5

<210> SEQ ID NO 19
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp(Mop)-sr

<400> SEQUENCE: 19

Leu Tyr Arg Ala Asp
 1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp(alpha)

<400> SEQUENCE: 20

Leu Tyr Arg Ala Asp Cys Ser Tyr Arg Phe Leu
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Asp(OMop)

<400> SEQUENCE: 21

Leu Tyr Arg Ala Asp Cys Ser Tyr Arg Phe Leu
 1               5                  10
```

US 7,566,697 B2

CARBOXY PROTECTION STRATEGIES FOR ACIDIC C-TERMINAL AMINO ACIDS IN CHEMICAL LIGATION OF OLIGOPEPTIDES

CROSS-REFERENCES TO RELATED APPLICATIONS

This application claims benefit of priority to U.S. Provisional Patent Application No. 60/387,825, filed Jun. 10, 2002.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE PRESENT INVENTION

The sequencing of the human genome has created the promise and opportunity for understanding the function of all genes and proteins relevant to human biology and disease, Peltonen and McKusick, Science, 291: 1224-1229 (2001). However, several important hurdles must be overcome before this promise can be fully attained. First, even with the human genome sequence available, it is still difficult to distinguish genes and the sequences that control their expression. Second, although monitoring gene expression at the transcript level has become more robust with the development of microarray technology, a great deal of variability and control of function originates in post-transcriptional events, such as alternative splicing and post-translational processing and modification. Finally, because of the scale of human molecular biology, potentially many tens of thousands of genes, and their expression products, will have to be isolated and tested in order to understand their role in health and disease, Dawson and Kent, Annu. Rev. Biochem., 69: 923-960 (2000).

In regard to the issue of scale, the application of conventional recombinant methodologies for cloning, expressing, recovering, and isolating proteins is still a time consuming and labor-intensive process, so that its application in screening large numbers of different gene products for determining function has been limited. Recently, a synthesis approach has been developed which can address the need for facile access to highly purified research-scale amounts of protein for functional screening, Dawson and Kent (cited above) and Dawson et al., Science, 266: 776-779 (1994). In its most attractive implementation, an unprotected oligopeptide intermediate having a C-terminal thioester reacts with an N-terminal cysteine of another oligopeptide intermediate under mild aqueous conditions to form a thioester linkage which spontaneously rearranges to a natural peptide linkage, Kent et al., U.S. Pat. No. 6,184,344. The approach has been used to assemble oligopeptides into active proteins both in solution phase, e.g. Kent et al., U.S. Pat. No. 6,184,344, and on a solid phase support, e.g. Canne et al., J. Am. Chem. Soc., 121: 8720-8727 (1999). Recently, the technique has been extended to permit coupling of C-terminal thioester fragments to a wider range of N-terminal amino acids of co-reactant peptides by using a removable ethylthio moiety attached to the N-terminal nitrogen of the co-reactant, thereby mimicking the function of an N-terminal cysteine, Low et al., Proc. Natl. Acad. Sci., 98: 6554-6559 (2001).

Despite these advances, such peptide couplings have low yields as a result of undesired rearrangements between atoms in the side chain and those in the thioester moiety of an acidic C-terminal amino acid. This greatly limits the applicability of the generalized native ligation chemistries. Therefore, the field of protein synthesis would be advanced if the reasons for such low yields were understood and approaches were found to overcome current limitations in reaction yield. Surprisingly, the present invention provides such understanding and solutions.

SUMMARY OF THE PRESENT INVENTION

In one aspect, the present invention provides a method of chemically ligating two oligopeptides, wherein a first oligopeptide thioester having an acidic C-terminal amino acid, the acidic C-terminal amino acid having a thioester moiety, a side chain, and a side chain protecting group such that the side chain protecting group substantially prevents rearrangements between atoms of the side chain and atoms of the thioester moiety, is contacted with a second oligopeptide having an N-terminal amino acid under chemical ligation conditions such that the thioester moiety of the first oligopeptide thioester ligates to the N-terminus of the second oligopeptide to form an oligopeptide or polypeptide product.

In another aspect, the present invention provides an oligopeptide thioester defined by the formula:

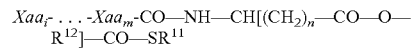

wherein each $Xaa_i$ is independently a protected or unprotected amino acid for i=1 to m; m is an integer from 2 to 70; n is an integer equal to 1 or 2; $R^{11}$ is a member selected from the group consisting of alkyl having from 1 to 6 carbon atoms, alkylaryl having from 6 to 8 carbon atoms, $-CH_2-CONH_2$, $-CH_2CH_2CONH_2$, and $-(CH_2)_k-CO-Xaa$, wherein subscript k is an integer equal to 1 or 2 and Xaa is an amino acid; and $R^{12}$ is a carboxy protecting group.

DETAILED DESCRIPTION OF THE PRESENT INVENTION

I. Definitions

Figure 1:
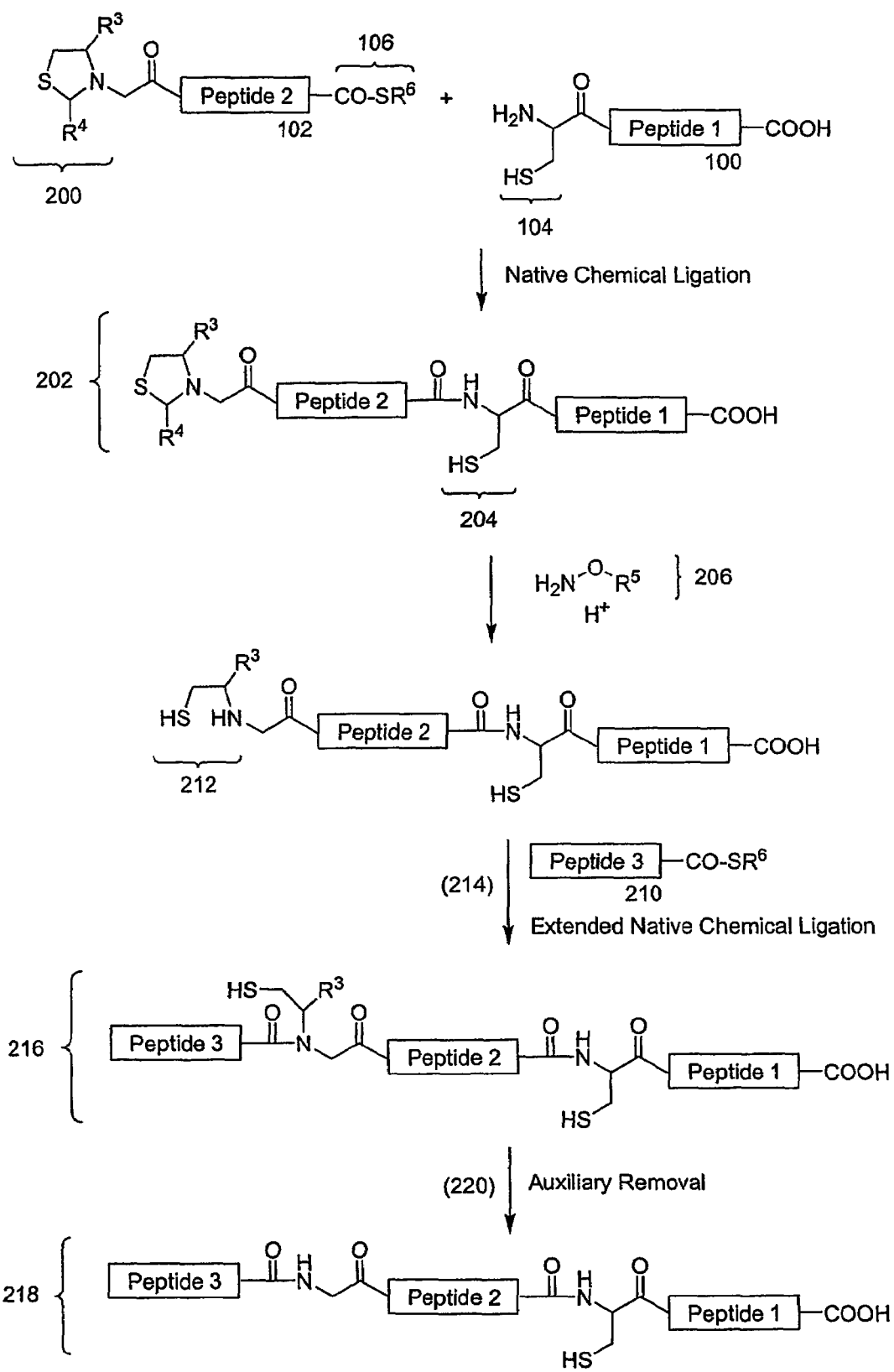
FIG. 1 illustrates native chemical ligation with the use of auxiliary groups ("extended native chemical ligation") using a heterocyclic-protected thioester-modified oligopeptide intermediate of the present invention.

As used herein, the terms "peptide," "peptide fragment," "oligopeptide," or "fragment" in reference to a peptide are used synonymously and refer to a compound made up of a single unbranched chain of amino acid residues linked by peptide bonds. Amino acid residues are sometimes represented herein by the symbol "$Xaa_i$," where "i", when present, designates the position of the amino acid within a peptide. Each $Xaa_i$ is independently selected from the group of natural and non-natural amino acids. Amino acids in a peptide or oligopeptide can be derivatized with lipid moieties, polyethylene glycol, dyes, biotin, haptens, oligonucleotides, or like moieties. The number of amino acid residues in such compounds varies widely. Peptides or oligopeptides referred to herein preferably have from 2 to 70 amino acid residue. More preferably, peptides or oligopeptides referred to herein have from 2 to 50 amino acid residues.

As used herein, the term "protein" is used synonymously with the term "polypeptide", or can refer to, in addition, a complex of two or more polypeptides which can be linked by bonds other than peptide bonds, for example, such polypeptides making up the protein can be linked by disulfide bonds. The term "protein" can also include a family of polypeptides having identical amino acid sequences but different post-translational modifications, such as phosphorylations, acylations, glycosylations, and the like. In particular, these post-translational modifications can be added when such proteins are expressed in eukaryotic hosts. Polypeptides and proteins referred to herein usually have from a few tens of amino acid residues, e.g. 20, to up to a few hundred amino acid residues, e.g. 200, or more.

Amino acid residues are referred to herein by their standard single-letter or three-letter notations: A, alanine; C, cysteine; D, aspartic acid; E, glutamic acid; F, phenylalanine; G, glycine; H, histidine; I, Isoleucine; K, lysine; L, leucine; M, methionine; N, asparagine; P, proline; Q, glutamine; R, arginine; S, serine; T, threonine; V, valine; W, tryptophan; and Y, tyrosine. An amino acid sequence set forth herein, such as "DKLLM," (SEQ ID NO: 1) orders the amino acids from the N-terminus to the C-terminus in a left-to-right manner, unless otherwise indicated from the context. One of skill in the art will appreciate that non-natural amino acids are also useful in the present invention.

As used herein, the term "contacting" refers to the process of bringing into contact at least two distinct species such that they can react. In one embodiment, contacting an amine and an ester under appropriate conditions known to one of skill in the art would result in the formation of an amide.

As used herein, "electron withdrawing" refers to the tendency of a substituent to attract valence electrons from the molecule to which it is attached, i.e. it is electronegative, and "electron donating" refers to the tendency of a substituent to donate valence electrons to the molecule to which it is attached, i.e. it is electropositive, e.g., Smith and March, March's Advanced Organic Chemistry: Reactions, Mechanisms, Structure, $5^{th}$ Edition (Wiley-Interscience, New York, 2001). Preferred electron withdrawing substituents are halogen, substituted or unsubstituted amides, substituted or unsubstituted sulfonamides, substituted or unsubstituted benzyl, substituted or unsubstituted hydroxy-amine, polyhaloalkyl, hydrazide, cyano, nitro and quaternary ammonium salts, or alkyl groups having 1 to 3 carbons and substituted with one or more of the above substituents, aryl groups substituted with one or more of the above substituents, substituted or unsubstituted esters, or substituted or unsubstituted thioesters. More preferably, electron withdrawing substituents are halo-substituted methyl. Preferred electron donating substituents include alkyl having from 1 to 3 carbon atoms, methoxy, thiol, hydroxyl, and methylthio. More preferably, electron donating substituents are methoxy, thiol, methylthio, or hydroxyl. Preferably, whenever a substituents is substituted with an electron-donating group or an electron-withdrawing group, such as electron donating- or electron-withdrawing-substituted phenyl, between 1 and 3 such groups are attached. More preferably, between 1 and 2 such groups are attached.

As used herein, the term "chemically ligating" refers to the joining of two oligopeptides to form a single product, such as another oligopeptide, a polypeptide, or a protein, for example.

II. General

In one aspect, the present invention derives from the discovery of a mechanism that leads to mixed reaction products in chemical ligation reactions involving reactants with acidic C-terminal amino acids. In particular, it was discovered that a high percentage of undesired side products are generated in such reactions due to rearrangements among the atoms of the side chain of the acidic C-terminal amino acid and those of the terminal thioester of one of the reactants. Acidic amino acids, such as glutamic acid and aspartic acid, at the C-terminus of the thioester reactant, generate the following class of side product in a native chemical ligation reaction:

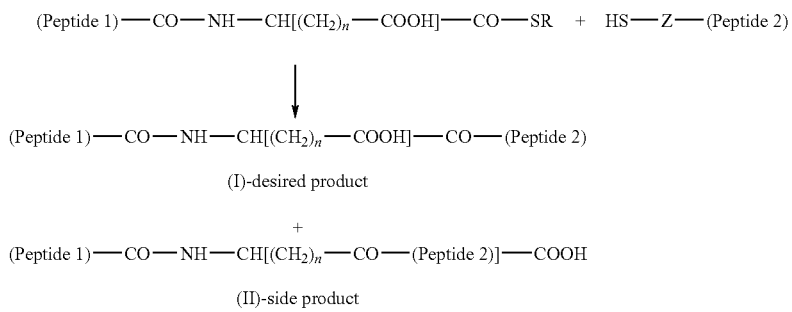

where n is 1 or 2, and Z is a bond when the N-terminal amino acid of Peptide 2 is cysteine or a removable thiol group that mimics the function of cysteine.

It has now been discovered that the production of undesired product (II) can be substantially prevented by employing a protecting group for acidic C-terminal amino acids that has the following properties: i) it must be stable to the conditions used to synthesize and cleave the oligopeptide from a synthesis resin when solid phase methods are employed; ii) it must be stable to the conditions used in the chemical ligation reaction; and iii) it must be removable after a native chemical ligation has been completed.

In view of the above, the objects of the present invention include, but are not limited to, providing improved methods for chemical synthesis of oligopeptides and polypeptides; providing methods of protecting oligopeptide intermediates that can undergo native chemical ligation to form an oligopeptide or polypeptide product; providing methods of protecting acidic C-terminal amino acid thioesters in native chemical ligation reactions to prevent the generation of undesired side products; providing methods of preventing undesirable rearrangements of atoms in the side chain of an acidic C-terminal amino acid with those of a thioester in a peptide thioester; and providing methods for chemically ligating in high yield a peptide thioester having an acidic C-terminal amino acid to the N-terminus of another peptide.

The present invention is useful in methods for synthesis of oligopeptides, polypeptides and proteins, and advantageously addresses limitations in these methodologies. In particular, it provides methods and materials for improving the efficiency of native chemical ligation reactions used to assemble thioester-modified oligopeptides into oligopeptides, polypeptides or proteins, particularly in such reactions involving oligopeptide thioesters having acidic C-terminal amino acids.

III. Methods of Preparing Oligopeptides Via Chemical Ligation

The present invention provides methods for the assembly of oligopeptides into an oligopeptide or polypeptide by the process of native chemical ligation. Related methods are described by Dawson et al., Science, 266: 776-779 (1994); Low et al., Proc. Natl. Acad. Sci., 98: 6554-6559 (2001) and Botti et al, Tetrahedron Letters, 42: 1831-1833 (2001). In particular, the present invention provides methods and compositions for carrying out native chemical ligation reactions at higher yields whenever oligopeptide thioester reactants are employed that have an acidic C-terminal amino acid. The present invention achieves this objective by providing a side chain protecting group for the acidic C-terminal amino acid, wherein the side chain protecting group substantially prevents undesired rearrangements between atoms in the side chain and those in the thioester moiety.

In one aspect, the present invention provides a method of chemically ligating two oligopeptides, wherein a first oligopeptide thioester having an acidic C-terminal amino acid, the acidic C-terminal amino acid having a thioester moiety, a side chain, and a side chain protecting group such that the side chain protecting group substantially prevents rearrangements between atoms of the side chain and atoms of the thioester moiety, is contacted with a second oligopeptide having an N-terminal amino acid under chemical ligation conditions such that the thioester moiety of the first oligopeptide thioester ligates to the N-terminus of the second oligopeptide to form an oligopeptide or polypeptide product.

In a preferred aspect, the side chain protecting groups of the present invention substantially prevent rearrangements between atoms of the side chain and atoms of the thioester moiety of the present invention. The term "substantially prevents" refers to the minimization of the rearrangement between the atoms of the side chain and the atoms of the thioester moiety. In a preferred aspect, the rearrangement occurs less than 10% of the time. In a more preferred aspect, the rearrangement occurs less than 5% of the time. In a most preferred aspect, the rearrangement occurs less than 1% of the time.

In another preferred aspect, the present invention provides a method of chemically ligating an oligopeptide thioester having an acidic C-terminal amino acid to the N-terminus of another oligopeptide to form an oligopeptide or polypeptide product, wherein the side chain protecting group is selected from the group consisting of 9-fluorenylmethyl ester, (phenylsulfonyl)ethyl ester, 2,2,2-trichloroethyl ester, and a phenacyl ester. In a more preferred aspect, the present invention provides a method of chemically ligating two oligopeptides to form an oligopeptide or polypeptide product, wherein the side chain protecting group is a phenacyl ester having the formula:

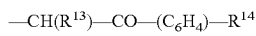

—CH($R^{13}$)—CO—($C_6H_4$)—$R^{14}$ wherein $R^{13}$ and $R^{14}$ are each electron-donating groups. In a further preferred aspect, the present invention provides a method of chemically ligating two oligopeptides to form an oligopeptide or polypeptide product, wherein $R^{13}$ and $R^{14}$ are each alkyl having from 1 to 3 carbon atoms. In yet another preferred aspect, the present invention provides a method of chemically ligating two oligopeptides to form an oligopeptide or polypeptide product, wherein $R^{13}$ is methyl or ethyl.

In another aspect, the present invention provides methods of chemically ligating a first oligopeptide thioester having an acidic C-terminal amino acid to the N-terminus of a second oligopeptide to form an oligopeptide or polypeptide product, wherein the N-terminal amino acid of the second oligopeptide is cysteine or an amino acid with a removable ethylthiol moiety. In a preferred aspect, the present invention provides methods of chemically ligating a first oligopeptide thioester having an acidic C-terminal amino acid to the N-terminus of a second oligopeptide to form an oligopeptide or polypeptide product, wherein the second oligopeptide with an N-terminal amino acid having a removable ethylthiol moiety, has the following formula:

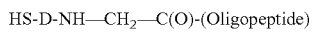

HS-D-NH—$CH_2$—C(O)-(Oligopeptide)

wherein D is an optionally substituted ethylene group, as defined below.

In still another aspect, the present invention includes methods and oligopeptides for monitoring the presence of side product (II) in a ligation reaction mixture. Such method includes the steps of treating a sample of such ligation reaction with a protease that cleaves an oligopeptide or polypeptide adjacent to an Asp or a Glu; subjecting the treated sample to chromatography to produce a first chromatogram; subjecting an untreated sample to chromatography to produce a second chromatogram; and comparing the first and the second chromatograms to determine the relative amount of side product (II) in the reaction mixture.

A. Oligopeptide ligation chemistry

In the original native chemical ligation technique, e.g. as described by Dawson et al. and Kent et al., coupling of peptide fragments could take place only between an N-terminal cysteine and a C-terminal thioester. In Dawson et al. and Kent et al., a first oligopeptide is provided with an N-terminal cysteine having an unoxidized sulfhydryl side chain, and a second oligopeptide is provided with a C-terminal thioester. In the subsequent coupling reaction, the unoxidized sulfhydryl side chain of the N-terminal cysteine is condensed with the C-terminal thioester to produce an intermediate oligopeptide which links the first and second oligopeptides with a β-aminothioester bond. The β-aminothioester bond of the intermediate oligopeptide then undergoes an intramolecular rearrangement to produce the oligopeptide product that links the first and second oligopeptides via an amide bond.

A problem arises in this scheme when an oligopeptide or polypeptide is assembled from three or more fragments. In this situation, at least one fragment will have both an N-terminal cysteine and a C-terminal thioester, thereby creating the possibility for self-ligation, which under conventional reaction conditions is quite significant because of the close proximity of the reactive intra-molecular moieties. In view of this, the N-terminal cysteine of an internal fragment can be protected from such reactions by a cyclic thiazolidine protecting group, as demonstrated by Gaertner et al., Proceedings of the 17$^{th}$ American Peptide Symposium, pgs. 107-108 (San Diego, Jun. 9-14, 2001). These protecting group strategies, however, were previously unavailable to chemical ligations using auxiliary groups, such as disclosed by Low et al. and Botti et al.

In accordance with the present invention, a new class of heterocyclic protecting groups is provided that significantly increases the efficiency of ligations by preventing self-ligations in auxiliary groups-assisted ligations. The operation of the heterocyclic protecting groups is illustrated in FIG. I for a three component ligation. In FIG. 1, radical $R^4$ is such that it promotes the opening of the thiazolidine ring, $R^5$ is hydrogen or alkyl, $R^3$ is hydrogen or an electron-donating group, and $R^6$ is an alkyl linker to an amide or an amino acid. Heterocyclic-protected thioester-modified oligopeptide (102) has thioester group (106) and exemplary heterocyclic protecting group (200). Thioester (106) reacts with N-terminal cysteine (104) of oligopeptide (100) in a procedure similar to that described by Dawson et al., Kent et al., and others (cited above) to give ligation product (202) consisting of oligopeptide (100) and oligopeptide (102) conjugated by amide bond (204). The ligation product at this step is then treated with an O-alkoxy-hydroxylamine (206) under acidic conditions to open heterocyclic protecting group (200) affording a free terminal sulfhydryl group on auxiliary group (212), which is attached to the secondary amine of the N-terminal amino acid (208), which in this illustration is glycine. After such deprotection, the next thioester-modified oligopeptide (210) reacts (214) with N-terminal amine (208) in a procedure similar to that by Low et al. and Botti et al. (cited above) to provide the intermediate product (216). The auxiliary group (212) is removed (220) by acid treatment to afford the final product (218). Preferably, such removal is accomplished by treatment with HF or trifluoroacetic acid (TFA). Exemplary removal conditions include: (i) 95% HF and 5% p-cresol; (ii) TFA/bromotrimethylsilane; and (iii) 95% TFA, 2.5% triisopropylsilane (TIS), and 2.5% water. Other removal conditions will be apparent to one of skill in the art. Unless otherwise noted, these reactions and those described below take place at room temperature.

Figure 2:
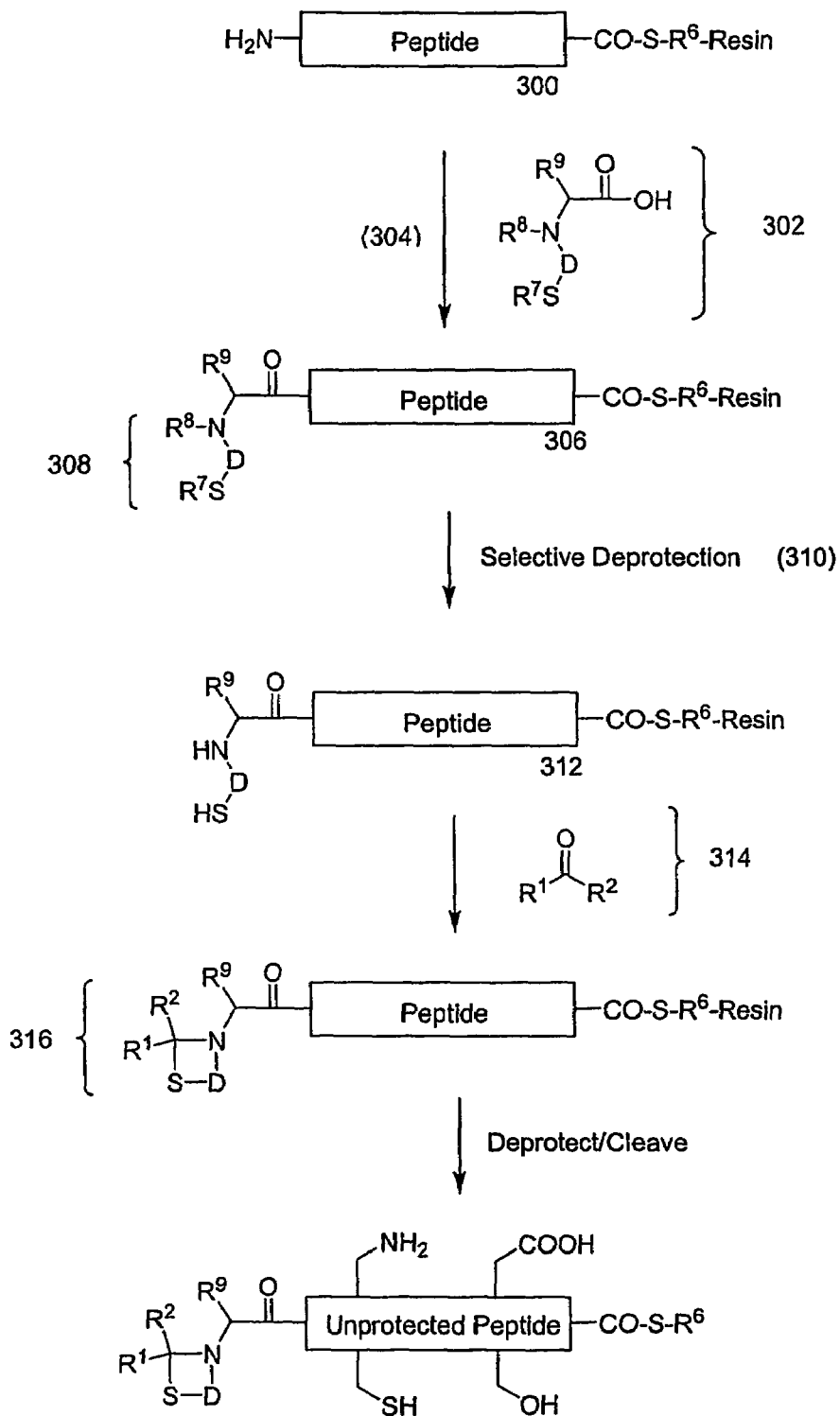
FIG. 2 illustrates a first scheme for synthesizing heterocyclic-protected thioester-modified oligopeptide intermediates of the present invention.
Figure 3:
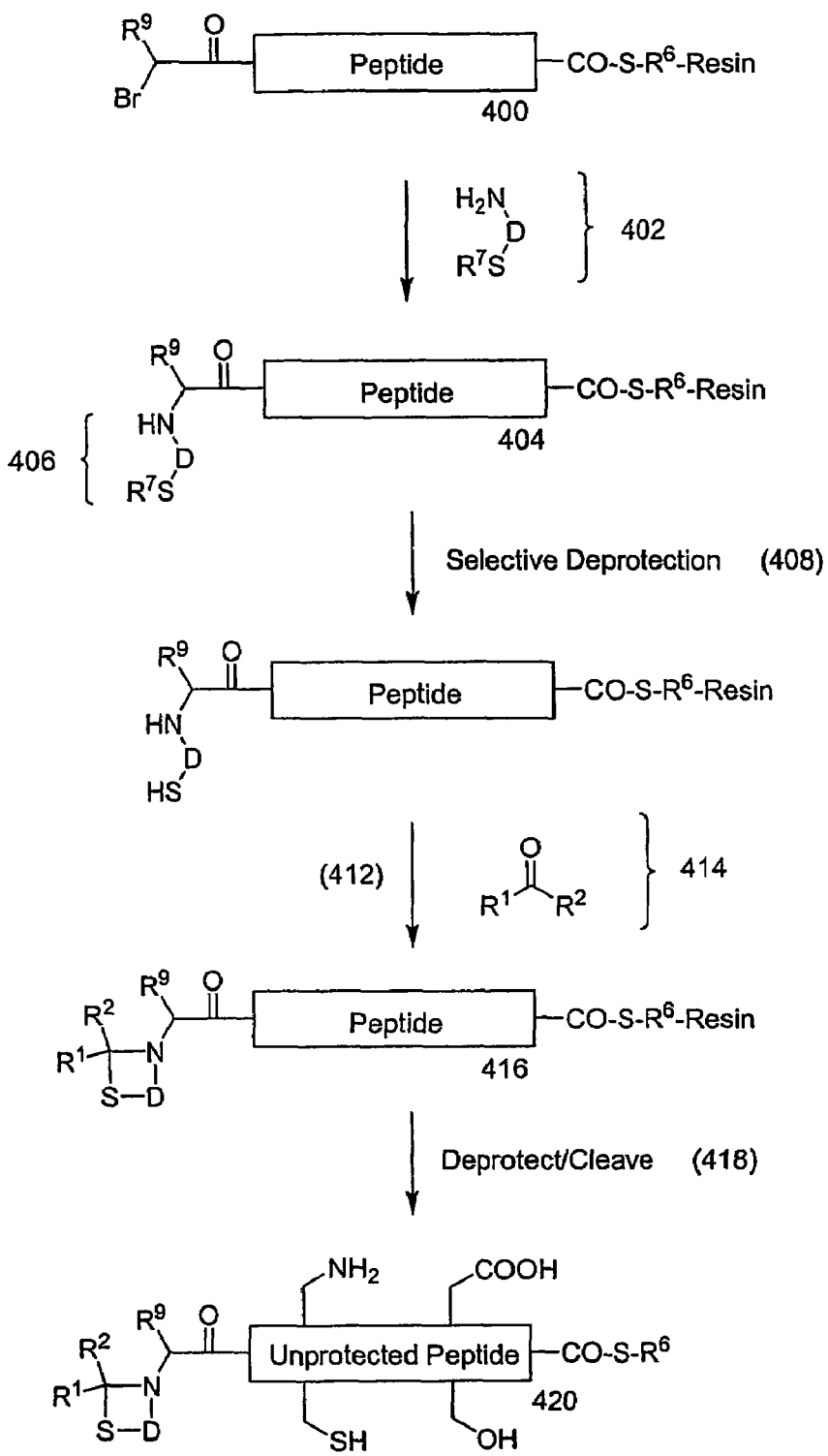
FIG. 3 illustrates a second scheme for synthesizing heterocyclic-protected thioester-modified oligopeptide intermediates of the present invention.
Figure 4:
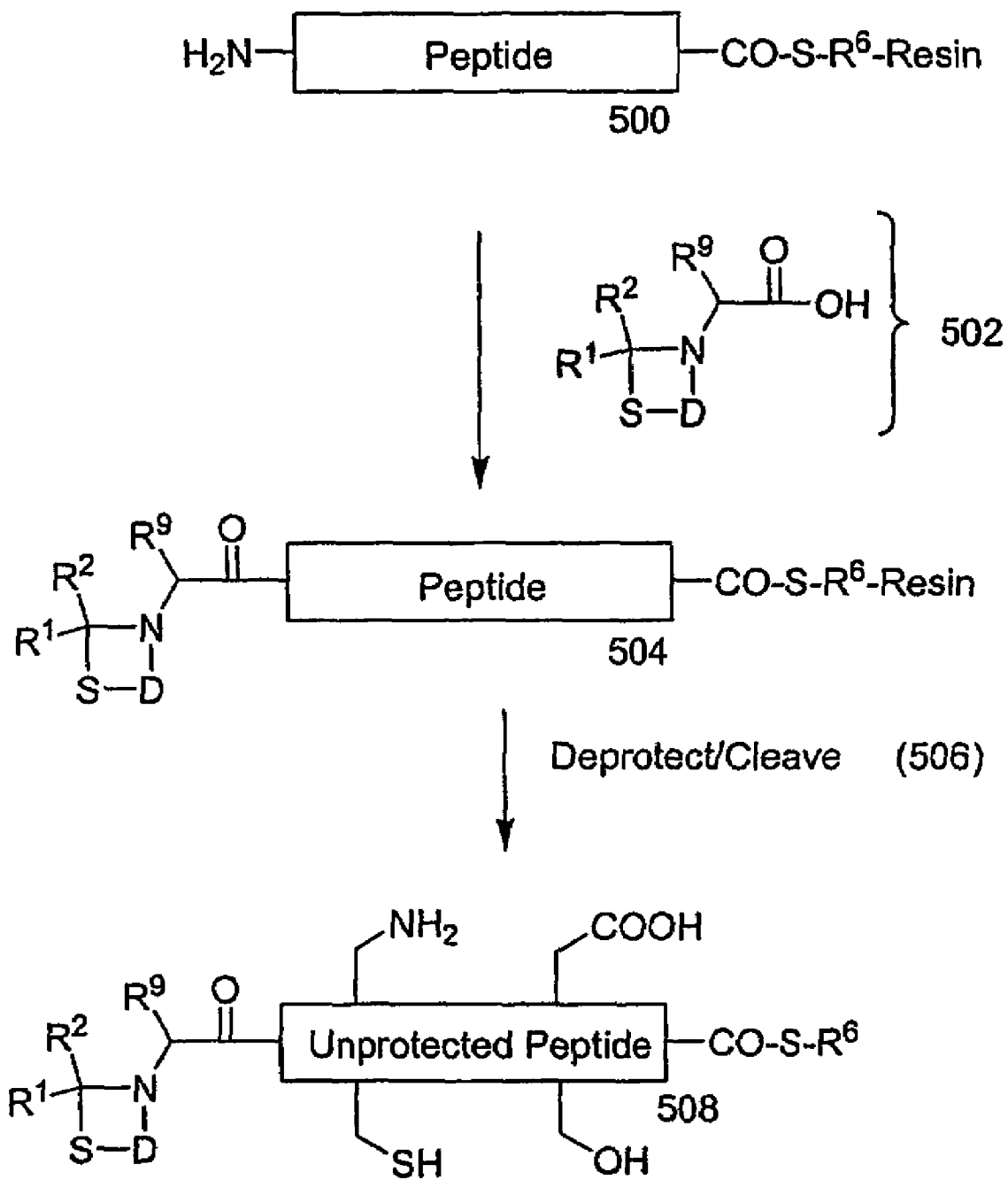
FIG. 4 illustrates a third scheme for synthesizing heterocyclic-protected thioester-modified oligopeptide intermediates of the present invention.
Figure 5:
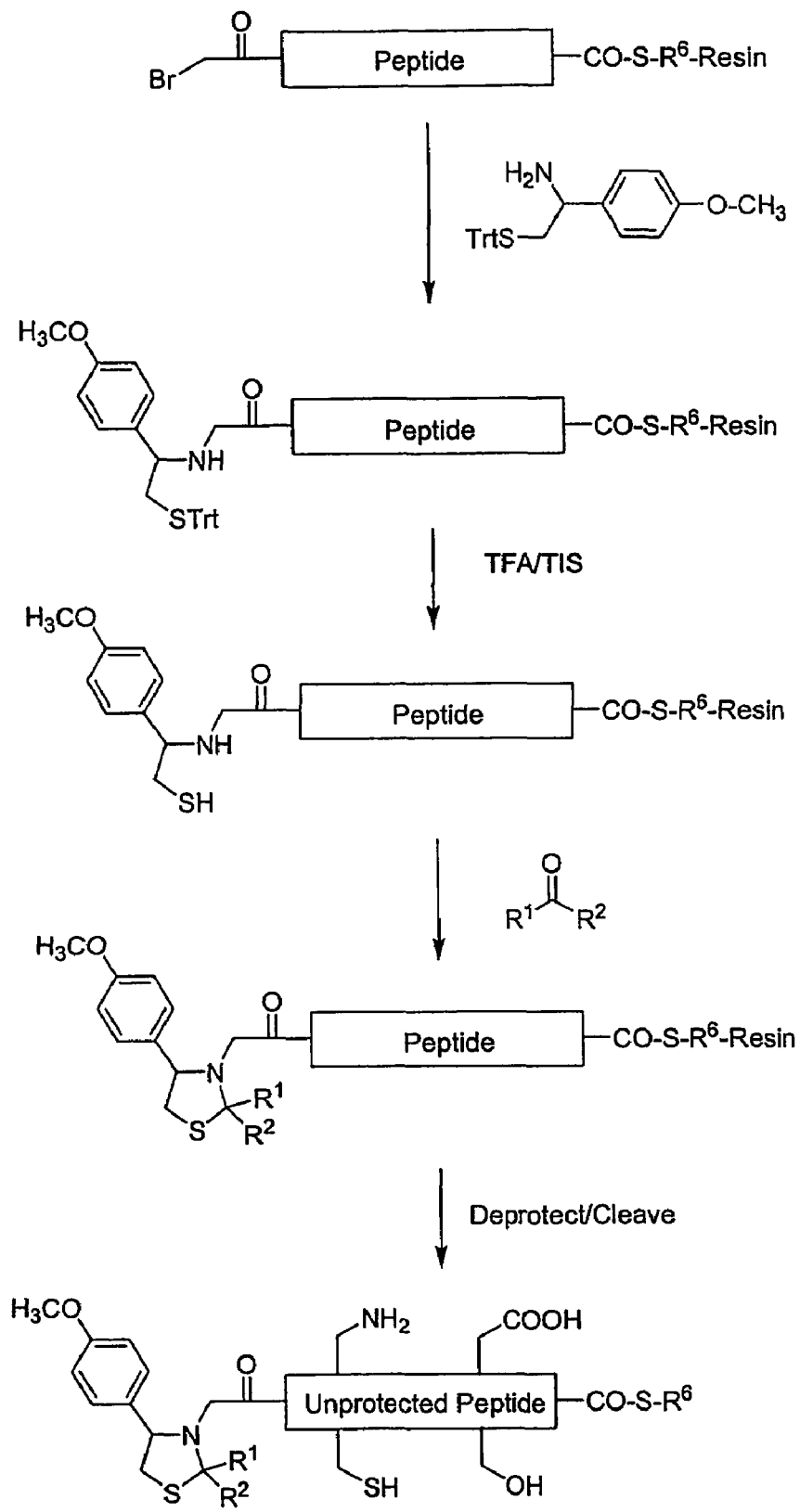
FIG. 5 illustrates a synthesis scheme for making a 4-substituted 1,3-thiazolidine-protected oligopeptide thioester.
Figure 6:
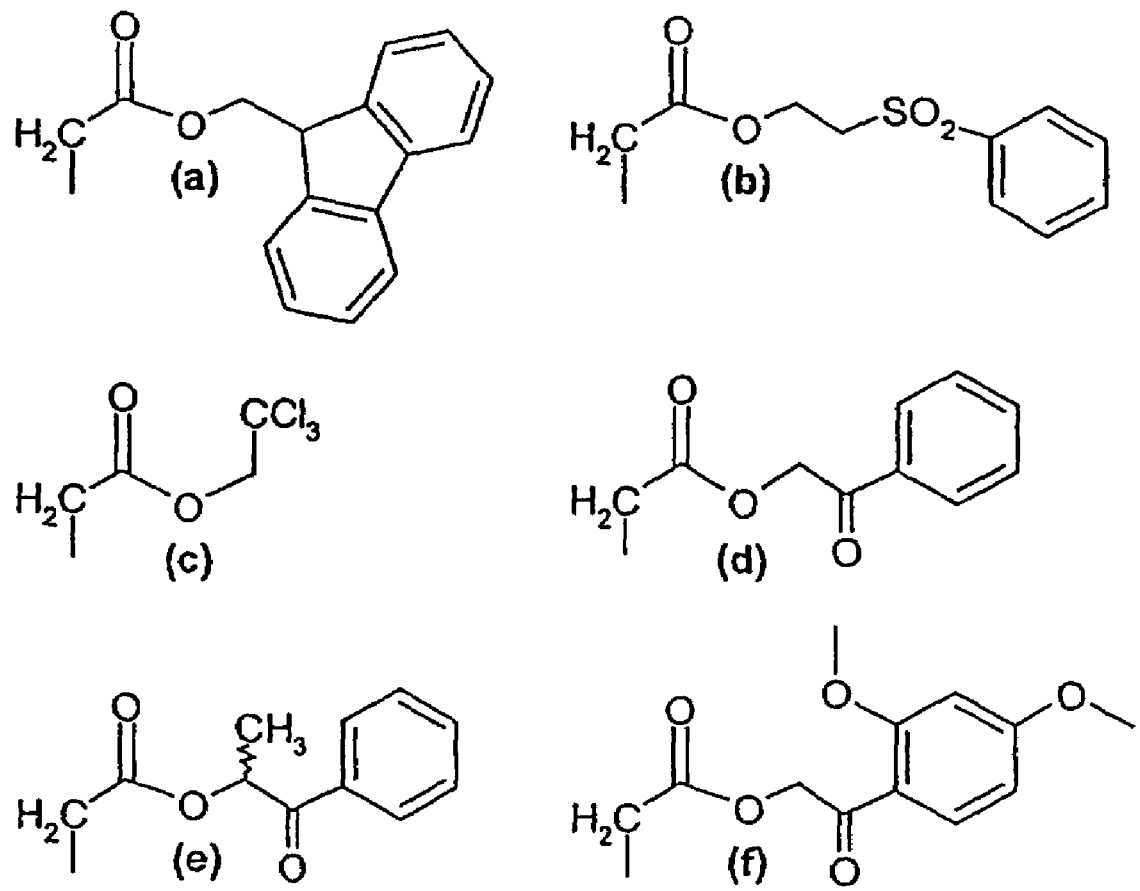
FIG. 6 illustrates several side-chain protecting groups that can be used in accordance with the present invention.

The heterocyclic protecting group (200) can be formed at the N-terminus of an oligopeptide thioester by first synthesizing the oligopeptide thioester with an auxiliary group (212) followed by cyclization of the free sulfhydryl of the auxiliary group with the secondary α-amine (208) of the terminal amino acid. An oligopeptide thioester having an auxiliary group can be synthesized in several ways, including by halogen-mediated amino alkylation or by reductive amination. Alternatively, the heterocyclic protecting group can be formed by preparation of a fully protected amino acid monomer with the heterocyclic protecting group in place for the last addition cycle in the synthesis of a desired oligopeptide thioester. Generally, however, synthesis begins with an oligopeptide thioester attached to a resin, as shown in FIGS. 2-4.

B. Solid Phase Synthesis of Oligopeptides

The oligopeptides prepared by the methods described above, can also be prepared on a suitable solid support member. A suitable solid phase support can be selected on the basis of desired end use and suitability for various synthetic protocols. For example, in polyamide synthesis, useful solid phase support can be resins such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp, Polymere, Tubingen, Germany), polydimethylacrylamide resin (available from Milligen/Biosearch, California), or PEGA beads (obtained from Polymer Laboratories).

Oligopeptides having a C-terminal thioester can be prepared following procedures similar to those described in the following references: Kent et al., U.S. Pat. No. 6,184,344; Tam et al., Proc. Natl. Acad. Sci., 92: 12485-12489 (1995); Blake, Int. J. Peptide Protein Res., 17: 273 (1981); Canne et al., Tetrahedron Letters, 36: 1217-1220 (1995); Hackeng et al., Proc. Natl. Acad. Sci., 94: 7845-7850 (1997); or Hackeng et al., Proc. Natl. Acad. Sci., 96: 10068-10073 (1999); Ingenito et al., J. Am. Chem, Soc., 121: 11369-11374 (1999).

Oligopeptides can be synthesized on a solid phase support typically on a 0.25 mmol scale by using the in situ neutralization/HBTU activation procedure for Boc chemistry, following a procedure similar to that disclosed by Schnolzer et al., Int. J. Peptide Protein Res., 40: 180-193 (1992). (HBTU is 2-(1H-benzotriazol-1-yl)-1,1,3,3-tetramethyluronium hexafluorophosphate and Boc is tert-butoxycarbonyl). Each synthetic cycle consists of N$^\alpha$-Boc removal by a 1- to 2-minute treatment with neat TFA, a 1-minute DMF flow wash, a 10- to 20-minute coupling time with 1.0 mmol of preactivated Boc-amino acid in the presence of DIEA, and a second DMF flow wash. (TFA is trifluoroacetic acid, DMF is N,N-dimethylformamide, and DIEA is N,N-diisopropylethylamine). N$^\alpha$-Boc-amino acids (1.1 mmol) are preactivated for 3 minutes with 1.0 mmol of HBTU (0.5 M in DMF) in the presence of excess DIEA (3 mmol). After each coupling step, yields are determined by measuring residual free amine with a conventional quantitative ninhydrin assay, e.g. as disclosed in Sarin et al., Anal. Biochem., 117: 147-157 (1981). After coupling of Gln residues, a DCM flow wash is used before and after deprotection by using TFA, to prevent possible high-temperature (TFA/DMF)-catalyzed pyrrolidone formation. Optionally, at the completion of chain assembly, a haloacetyl group, such as bromoacetyl, can be added, in a procedure similar to that disclosed by Zuckerman et al., J. Am. Chem. Soc. 114: 10646-10647 (1992), as one route for synthesizing compounds of the present invention.

Oligopeptide thioesters of the present invention can be synthesized using either Fmoc or Boc chemistries. When Fmoc chemistry is employed, a 3-carboxypropanesulfonamide "safety catch" linker is used to generate the thioester. Thioester oligopeptides described above are preferably synthesized on a trityl-associated mercaptopropionic acid-leucine (TAMPAL) resin, made in a procedure similar to that disclosed by Hackeng et al. (1999), or comparable protocol. N$^\alpha$-Boc-Leu (4 mmol) is activated with 3.6 mmol of HBTU in the presence of 6 mmol of DIEA and coupled for 16 minutes to 2 mmol of p-methylbenzhydrylamine (MBHA) resin, or the equivalent. Next, 3 mmol of S-trityl mercaptopropionic acid is activated with 2.7 mmol of HBTU in the presence of 6 mmol of DIEA and coupled for 16 minutes to Leu-MBHA resin. The resulting TAMPAL resin can be used as a starting resin for polypeptide-chain assembly after removal of the trityl protecting group with two 1-minute treatments with 3.5% triisopropylsilane and 2.5% H$_2$O in TFA. The thioester bond can be formed with any desired amino acid by using standard in situ-neutralization peptide coupling protocols for 1 hour, in a procedure similar to that disclosed in Schnolzer et al. (cited above). Treatment of the final oligopeptide with anhydrous HF yields the C-terminal activated mercaptopropionic acid-leucine (MPAL) thioester oligopeptides.

In a preferred embodiment, oligopeptide thioesters are deprotected and cleaved from the resin by treatment with anhydrous HF for 1 hour at 0° C. with 4% p-cresol as a scavenger. The imidazole side-chain 2,4-dinitrophenyl (DNP) protecting groups remain on the His residues because the DNP-removal procedure is incompatible with C-terminal thioester groups. However, DNP is gradually removed by thiols during the ligation reaction. After cleavage, oligopeptide thioesters can be precipitated in ice-cold diethylether, dissolved in aqueous acetonitrile, and lyophilized.

C. Preparation of Heterocyclic Protected Oligopeptide Thioester Intermediates

Reaction of N-terminal Amines with Protected Amino Acids

Heterocyclic protected oligopeptide thioesters are synthesized by a variety of schemes, as illustrated in FIGS. 2-4. In Scheme 1, shown in FIG. 2, a free N-terminal amine of oligopeptide thioester (300) is reacted with protected amino acid (302), having auxiliary group (-D-S—$R^7$), in a standard coupling reaction (304), e.g. Schnolzer et al. (cited above), to afford oligopeptide thioester (306) having auxiliary group (308) attached to the α-amine. $R^9$ is an amino acid side chain, other than the side chain for proline. Preferably, $R^9$ is a non-sterically hindering amino acid side chain, or the side chain of histidine. More preferably, $R^9$ is hydrogen, methyl, hydroxymethyl, or the side chain of histidine. Oligopeptide thioester (312) is formed by selective deprotection (310) of the α-amine and the sulfhydryl group of the auxiliary group. In a preferred embodiment, selective deprotection (310) is achieved by mild acid treatment, for example, trifluoroacetic acid (TFA) under conventional reaction conditions, e.g. Green and Wuts (cited below), in the presence of a scavenger, such as triisopropylsilane (TIS), whenever $R^8$ is Boc, or like protecting group, and $R^7$ is triphenylmethyl, i.e. trityl, or like protecting group. Guidance for selecting appropriate amino and sulfhydryl protecting groups and $N^\alpha$ protecting groups for selective deprotection is found in Greene and Wuts, Protecting Groups in Organic Chemistry, 3rd Edition (John Wiley & Sons, New York, 1999). Following deprotection, the oligopeptide thioester (312) is reacted with substituted carbonyl (314) so that heterocyclic protecting group (316) is formed.

Exemplary $R^8$ protecting groups include t-butylcarbamate (Boc), 9-fluorenylmethylcarbamate (Fmoc), 4-nitrophenylethylsulfonyl-ethyloxycarbonyl (NSC), 2,2,2-trichloroethylcarbamate (Troc), bromobenzylcarbamate (BrZ), chlorobenzylcarbamate (ClZ), and the like. In a preferred embodiment, $R^8$ protecting groups are Boc and Fmoc.

Exemplary $R^7$ protecting groups include benzyl, 4-methylbenzyl, 4-methoxybenzyl, trityl, acetamidomethyl, trimethylacetamidomethyl, xanthyl, and the like. Further protecting groups useful in the present invention will be apparent to one of skill in the art.

In regard to the other substituents of the Figures, $R^1$ and $R^2$ are selected to promote the opening of the heterocyclic protecting group under acidic conditions in the presence of a nucleophilic agent. In a preferred embodiment, $R^1$ and $R^2$ are separately hydrogen, electron withdrawing-substituted alkyl having from 1 to 3 carbon atoms, alkylcarbonyl having 2 to 3 carbon atoms, or arylcarbonyl having 7 to 10 carbon atoms.

D is a linking moiety that together with a free sulfhydryl ("HS-D-") is referred to herein as an auxiliary group. In one aspect, D is an alkyl, alkenyl, aryl, aralkyl, cycloalkyl moiety having from 2 to 16 carbon atoms and from 0 to 4 heteroatoms that: (i) maintains the heterocyclic sulfur closely adjacent to the heterocylic nitrogen after deprotection in order to promote the rearrangement reaction of native chemical ligation; and (ii) provides a cleavable bond to the heterocyclic nitrogen so that after deprotection and fragment coupling, the auxiliary group is removed. In a preferred embodiment, whenever in the form "HS-D," D maintains the sulfhydryl group within an equivalent distance of 2 to 3 carbon-carbon bond lengths to the $N^\alpha$ of the N-terminal amino acid of the oligopeptide thioester reactant, the carbon-carbon bonds being those of a linear alkyl group. In a preferred aspect, the auxiliary group is an ethylthiol.

$R^3$ taken alone is hydrogen or an electron donating group having from 1 to 12 carbon atoms and from 0 to 4 heteroatoms selected from the group consisting of nitrogen, oxygen, sulfur, and phosphorus. Preferably, $R^3$ taken alone is hydrogen or electron donating group having from 1 to 8 carbon atoms and from 0 to 2 heteroatoms selected from the group consisting of nitrogen, oxygen, and sulfur. Still more preferred, $R^3$ taken alone is hydrogen, phenyl, electron donating-substituted phenyl, 2- or 4-picolyl, or electron donating-substituted 2- or 4-picolyl. Still more preferably, $R^3$ taken alone is hydrogen or methoxy-substituted phenyl. Most preferably, $R^3$ taken alone is 4-methoxyphenyl or 2,4-dimethoxyphenyl.

$R^6$ is alkyl having from 1 to 6 carbon atoms or alkylaryl having from 6 to 8 carbon atoms, —$CH_2$—$CONH_2$, —$CH_2CH_2CONH_2$, or —$(CH_2)_k$—CO-Xaa, wherein subscript k is an integer equal to 1 or 2 and Xaa is an amino acid.

$R^9$ is an amino acid side chain, other than those of proline and cysteine. More preferably, $R^9$ is an amino acid side chain other than those of proline, cysteine, valine, isoleucine, and-threonine. In further preference, $R^9$ is hydrogen, methyl, hydroxyrnethyl, or the side chain of histidine. Most preferably, $R^9$ is hydrogen or methyl.

Reaction of Bromoacetylated Oligopeptides with Auxiliary Group Precursors

A second scheme (Scheme 2) for synthesizing heterocyclic protected oligopeptide thioesters is shown in FIG. 3. This Scheme roughly follows the procedure disclosed by Botti et al. (cited above). Bromoacetylated oligopeptide thioester (400) is reacted with S-protected ethylamine or S-protected aminothiophenyl (402), or like group, to afford oligopeptide thioester (404) with auxiliary group (406), after which the sulfhydryl protecting group ($R^7$) is removed (408) with mild acid. In the case of $R^7$ being a trityl group, $R^7$ is removed with TFA in the presence of a trityl scavenger, such as TIS. The α-amine of oligopeptide thioester (410) and the free sulfhydryl of the auxiliary group are reacted (412) with carbonyl (414) to form a heterocyclic protected oligopeptide thioester (416). Preferably, carbonyl (414) is formaldehyde, acetaldehyde, acetone, or the like. More preferably, $R^1$=$R^2$ so that chiral forms are not produced. In some embodiments, it can be desirable to employ either or both $R^1$ and $R^2$ as an affinity or chromatography purification aid. For example, $R^1$ or $R^2$ can be biotin, digoxigenin, or like affinity group, connected to a linking moiety, e.g. biotin-$(CH_2)_n$—, or $R^1$ or $R^2$ can be a hydrophobic or hydrophilic group designed to modify chromatographic retention time to aid in purification. Heterocyclic protected oligopeptide thioester (416) is then deprotected and cleaved from the resin (418), e.g. by HF treatment, to give final product (420).

Reaction of N-terminal Amines with Auxiliary Group Derivatized Amino Acids

In a third Scheme (Scheme 3) shown in FIG. 4, the heterocyclic protecting group is added to the oligopeptide thioester by coupling a derivatized amino acid already having the group in place. Oligopeptide thioester (500) having a free N-terminal amine is reacted with a derivatized amino acid (502) in a conventional solid phase peptide synthesis reaction to afford oligopeptide (504), after which it is deprotected and cleaved (506) from the synthesis column to afford the final product (508). Derivatized amino acid (502) can be prepared by several routes. In a preferred embodiment, derivatived amino acid (502) is prepared by first synthesizing an intermediate having an auxiliary group-substituted $N^\alpha$ in the following nucleophilic substitution reaction:

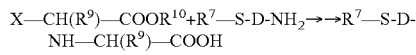

where X is halogen, preferably bromo, and $R^{10}$ is a conventional protecting group or a solid phase support. The sulfhydryl group of the resulting $N^\alpha$-substituted amino acid can be afforded by conventional protocols (e.g. TFA/TIS for trityl-protected sulfhydryl), after which it can be reacted with a substituted formaldehyde, $CO(R^1)(R^2)$, and the $N^\alpha$ amine to provide the derivatized amino acid (502). Alternatively, the above intermediate can be prepared via nucleophilic substitution or by reductive amination, as shown in the following reaction scheme:

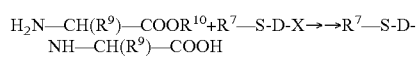

wherein X is a halogen for the nucleophilic substitution route, and X is a carbonyl for the synthesis via reductive amination. One of skill in the art will appreciate that when the product above is prepared via reductive amination (when X is a carbonyl), radical D of the product is chain extended by a single carbon atom. Accordingly, radical D in the starting material of the scheme above is a methylene or ethylene unit in some embodiments, and a direct bond in other embodiments.

In a preferred embodiment, heterocyclic-protected oligopeptide thioester intermediates are used in native chemical ligation under conditions similar to those described by Hackeng et al. (1999), or like conditions. 0.1 M phosphate buffer (pH 8.5) containing 6 M guanidine, 2% (vol/vol) benzylmercaptan, and 2% (vol/vol) thiophenol is added to dry peptides to be ligated, affording a final peptide concentration of 1-3 mM at about pH 7. In a preferred embodiment, the ligation reaction can be performed in a heating chamber at 37° C. under continuous stirring and can be periodically vortexed to equilibrate the thiol additives. The reaction can be monitored for degree of completion by MALDI-MS or HPLC and electrospray ionization MS.

Deprotection of N-terminal Amines and Removal of Auxiliary Groups

After a native chemical ligation reaction is completed or stopped, the N-terminal heterocyclic ring of the product can be opened by treatment with a deprotecting agent that is nucleophilic under acidic conditions. Such agents include certain O-alkylhydroxylamines, hydrazines, and like reagents. More preferably, the N-terminal heterocyclic ring of the product is opened by treatment with O-methylhydroxylamine (0.5 M) at pH 3.5-4.5 for 2 hours at 37° C., after which a 10-fold excess of Tris-(2-carboxyethyl)-phosphine (TCEP) is added to the reaction mixture to completely reduce any oxidizing reaction constituents prior to purification of the product. Preparative HPLC is the preferred method of purification. Preferably, fractions containing the ligation product are identified by electrospray MS, pooled, and lyophilized. Other reducing agents that can be used in place of Tris-(2-carboxyethyl)-phosphine include β-mercaptoethanolamine, dithiotreitol, and the like.

Returning to the deprotection strategies, N-terminal thiazolidines can be ring-opened with a variety of nucleophilic agents under acidic conditions, as discussed above. Ring-opening under acidic conditions is dependent on the C2 substituents (Wohr et al., J. Am. Chem. Soc., 118: 9218 (1994)).

The following agents can be used as thiazolidine ring-opening agents: O-methylhydroxylamnine and other hydroxylamine derivatives. Hydrazine or any of its derivatives, as well as thiosemicarbazides, which are nucleophilic under acidic conditions, can also be used, but this family of reagents is generally more toxic than the former, and the condensation product (hydrazone, thiosemicarbazone, respectively) is less stable than the oxime. Preferably, Tris-(2-carboxyethyl)-phosphine (TCEP), or like reducing agent, is used in the deprotection reaction to rapidly and stoichiometrically reduce most peptides and sulfhydryls even under acidic conditions (Burns et al., J. Org. Chem., 56: 2648-2650, 1991). Preferably, O-methoxyhydroxylamine is used as the thiazolidine ring-opening agent. O-methoxyhydroxylamine reacts with the masked aldehyde function in the thiazolidine ring to form an oxime, as shown below:

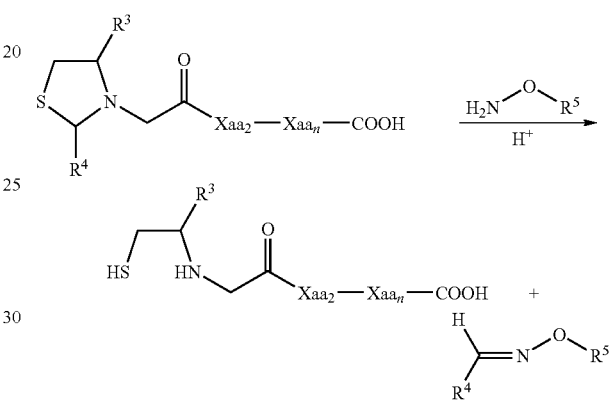

wherein $R^3$ is as defined above, and $R^4$ and $R^5$ can be, for example, hydrogen, alkyl, amide, ester, halogen, cycloalkyl, heterocyclyl, aryl and heteroaryl, all optionally substituted. In a preferred embodiment, $R^4$ promotes the deprotection of the thiazolidine ring. Such substituents will be apparent to one of skill in the art. One of skill in the art will appreciate that other agents can also be used to deprotect thiazolidine protecting groups of the present invention.

Auxiliary groups can be removed after each ligation step, or they can be removed all at the same time after the polypeptide final product is completely synthesized. Depending on the structure of the linking moiety "D" a variety of removal procedures are available. In the preferred form of D that donates electrons to the $N^\alpha$ of the adjacent amino acid, removal of the auxiliary group can be readily effected by acidic conditions, such as used in conventional peptide synthesis for side chain deprotection. Exemplary acids for such cleavage include HP, TFA, trifluoromethanesulfonic acid (TFMSA), and the like. In some embodiments, conventional scavenging agents, e.g. 5% p-cresol, or the like, can be used to bind or react with aryl, thiol, or other reactive moieties, and to prevent undesired secondary reactions with amino acid side chains.

After the synthesis is completed and the final product purified, the final polypeptide product can be refolded by conventional techniques similar to those described by Creighton, Meth. Enzymol., 107: 305-329 (1984); White, Meth. Enzymol., 11: 481-484 (1967); Wetlaufer, Meth. Enzymol., 107: 301-304 (1984); Misawa et al., Biopolymers, 51: 297-307 (1999); Anfinsen, Science, 181: 223-230 (1973); and the like. Preferably, a final product is refolded by air oxidation by dissolving the reduced lyophilized product (at about 0.1 mg/mL) in 1 M guanidine hydrochloride (or like chaotropic agent) with 100 mM Tris, 10 mM methionine, at pH 8.6. After gentle overnight stirring, the re-folded product is isolated by reverse phase HPLC with conventional protocols.

D. Side-Chain Protecting Groups

Oligopeptide thioester precursors having acidic C-terminal amino acids with protected side chains are produced by solid phase synthesis as described above. The side chain of the acidic C-terminal amino acid monomer is protected prior to use in synthesis using conventional chemistry, e.g. Greene and Wuts, Protective Groups In Organic Synthesis, Second Edition (John Wiley & Sons, New York, 1991). Typically, a protecting ester is formed in a nucleophilic displacement by a carbonyl hydroxyl of a halogen in a protecting group precursor, e.g. $(C_6H_5)COCH_2Br$ in the case of phenacyl ester protection. Protection is typically removed via a nucleophilic displacement under basic conditions in an aprotic solvent. Other suitable protection strategies are known to one of skill in the art.

IV. Oligopeptides and Polypeptides

In another aspect, the present invention provides an oligopeptide thioester defined by the formula:

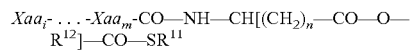
$$Xaa_i\text{-}\ldots\text{-}Xaa_m\text{-}CO\text{—}NH\text{—}CH[(CH_2)_n\text{—}CO\text{—}O\text{—}R^{12}]\text{—}CO\text{—}SR^{11}$$

wherein each $Xaa_i$ is independently a protected or unprotected amino acid for i=1 to m; m is an integer from 2 to 70; n is an integer equal to 1 or 2; $R^{11}$ is a member selected from the group consisting of alkyl having from 1 to 6 carbon atoms, alkylaryl having from 6 to 8 carbon atoms, —$CH_2$—$CONH_2$, —$CH_2CH_2CONH_2$, and —$(CH_2)_k$—CO-Xaa, wherein subscript k is an integer equal to 1 or 2 and Xaa is an amino acid; and $R^{12}$ is a carboxy protecting group.

In a preferred aspect, the present invention provides an oligopeptide thioester wherein $R^{12}$ is selected from the group consisting of 9-fluorenylmethyl ester, (phenylsulfonyl)ethyl ester, 2,2,2-trichloroethyl ester, and a phenacyl ester. In a more preferred aspect, the present invention provides an oligopeptide thioester wherein $R^{12}$ is a phenacyl ester defined by the formula:

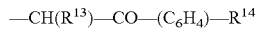
$$\text{—}CH(R^{13})\text{—}CO\text{—}(C_6H_4)\text{—}R^{14}$$

wherein $R^{13}$ and $R^{14}$ are each an electron-donating group.

In another aspect, whenever n is 1, $R^{12}$ is preferably a phenacyl ester. More preferably, whenever n is 1, $R^{12}$ is a phenacyl ester defined by the formula:

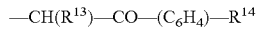
$$\text{—}CH(R^{13})\text{—}CO\text{—}(C_6H_4)\text{—}R^{14}$$

wherein $R^{13}$ is an electron-donating group and $R^{14}$ is an electron-donating group. Preferably, $R^{13}$ is an electron-donating group having from 1 to 3 carbon atoms and $R^{14}$ is attached to the phenyl moiety in an ortho- or para-configuration with respect to the carbonyl carbon also attached to phenyl moiety, —$(C_6H_4)$—. More preferably, $R^{13}$ is straight-chain alkyl having from 1 to 3 carbon atoms. Still more preferably, $R^{13}$ is methyl or ethyl.

V. EXAMPLES

In the following Examples, oligopeptide thioesters having acidic C-terminal amino acids were prepared with side chain protecting groups and ligated to the N-terminus of another oligopeptide. Reaction yields were tested by HPLC and digestion with SV8 protease. Side-chain protecting groups tested for Glu and Asp are illustrated in FIG. 4: (a) OFm, (b) OPse, (c) Troc, (d) Opac, (e) OMop and (f) OdiMeOPac.

A. Materials

Amino acid protection used for Boc chemistry peptide/synthesis were, Tyr(2BrZ)OH, Arg(Tos), Asp(OChx), Glu (OChx), Cys(pMeBzl), Ser(Bzl). Boc amino acids were obtained from Orpegen Pharma (Heidelberg, Germany). HBTU was from Luxemburg Science. All the chemicals were synthetic grade from Fluka or Aldrich (Buchs, Switzerland) and used as obtained. DIEA was from Applied Biosystems (Foster City, Calif.). Boc-Asp(OPse)-OH.DCHA and Boc-Glu(OPse)-OH.DCHA were from A&PEP Inc. (Bucheon, Korea). SV8 protease (Type XVII-B) was from Sigma (Buchs, Switzerland).

B. Solid Phase Synthesis of Oligopeptides

All peptides were prepared by solid phase synthesis using machine-assisted protocols on an Applied Biosystems model 433A peptide synthesizer, using in situ neutralization/2-(1H-Benzotriazole-1-yl)-1,1,3,3,tetramethyluronium hexafluorophosphate (HBTU) activation procedure for Boc chemistry as described [Schnölzer M., et al. *Int J Pept Protein Res.* 1992; 40: 180-193]. C-terminal peptides were synthesized on the appropriate Boc-aminoacyl-OCH$_2$-Pam preloaded resin. C-terminal Asp or Glu thioesters peptide were synthesized starting from the MPAL resin (β-mercapto-propionic acid-leucine) following a published procedure using PyBop as the activator [Hojo H, Aimoto S. *Bull. Chem. Soc. Jpn.* 1991; 64:111-117; Hojo H., et al. Bull. Chem. Soc. Jpn. 1993; 66:2700-2706]. Before activation, DCHA salts of BocAsp (OPse)OH and BocGlu(OPse)OH were transformed in the corresponding free acid by solubilizing the amino acid in 1M KHSO$_4$ and extracting the aqueous phase with ethyl acetate. The organic phase was dried under vacuum and the solid product solubilized in DMF and activated with PyBop.

After chain assembly was completed, the peptides were deprotected and simultaneously removed from the resin by treatment with anhydrous HF containing 5% p-cresol, lyophilized, and purified by preparative RP-HPLC on a Waters 600 HPLC module, using a C18 Waters DeltaPak preparative column. Peptide identity was confirmed by ESI spectroscopy on a Bruker Esquire 3000 Ion Trap (Brucker Daltonics, Bremen, Del.).

Analytical RP-HPLC of all the products was performed on a Waters 2690 HPLC module with 214 nm UV detection, using a Symmetry 300 C18 column, with a linear gradient of buffer B in buffer A over 30 minutes at 1 ml/min. Buffer A=0.1% TFA in water; buffer B=0.1% TFA in acetonitrile. Data were recorded and analyzed using the software system Millennium 32.

C. Ligation Reaction

The C-terminal unprotected peptide (1.5 equivalent) and the N-terminal peptide (1 equivalent) were solubilized in freshly degassed 6M guanidinium hydrochloride, 0.2 M sodium phosphate, pH 7.5 buffer at a concentration of 2.5 mM each. After addition of 1% thiophenol and 1% benzyl mercaptan the pH was adjusted to 6.5 (or different thiols concentration or pH as reported in the text). Aliquots of this solution were treated with equal volumes of BME for 5 minutes and then with 10% TCEP for 10 minutes to completely hydrolyse any thiol adduct before HPLC analysis. Ligation reaction analysis was conducted using a gradient starting from 10% of B with a gradient slope of 1.66% of B per minute. Base line resolution of the different isomerization product was achieved using a gradient starting at 20% of B and with an increase of 0.33% B.

D. Enzyme Digestion

Peptides were digested using the enzyme SV8 protease. The peptides, solubilized to a final 5 mM concentration in 0.1 M $NH_4HCO_3$ and 0.3% BME, were digested by adding the enzyme solution (250 unit/ml), keeping the enzyme/peptide ratio of 1 unit/20 μg. The reaction was stopped after 24 hours at 37° C. by treatment with equal volumes of 10% TCEP, and extent of digestion assayed by RP-HPLC. Digested fragments were characterized by ESI-MS.

E. Synthesis of Protected Asp Peptides

Synthesis of the different test Asp protected test peptides was achieved using Boc chemistry to synthesize the sequence YAKYAKL-Pam (SEQ ID NO: 2). Following tyrosine incorporation, the resin was deprotected with TFA and FmocAsp ($^t$Bu) was inserted. This was followed by piperidine deprotection (except for Troc), treatment with acetic anhydride, and .sup.tBu removal with TFA. After t-butyl removal, the resin was washed with DMF and the free carboxylic group protected on solid phase. For Troc, the resin was treated with 2,2,2-trichloroethanol (40 eq. of the resin free carboxylic acid), DMAP (0.1 eq.), NMM (1 eq.) and PyBop (1 eq.) in DMF overnight at 37° C. For OPac, OMop and diMeOPac, the resin was reacted with the corresponding α-bromo ketones, respectively phenacyl bromide, α-bromo-propiophenone and 2-bromo-2'-4'dimethoxyacetophenone. The same protocol was used for the three products, using an excess of 20 equivalents of the bromo-ketone over the resin free carboxylic acid with 1 equivalent of DIEA in DMF overnight at room temperature. The final products were cleaved and deprotected by HF treatment. The peptides were purified by preparative HPLC. OMop generated two diastereoisomers resolved by HPLC, only the major product was used. In general the yield of this procedure was 45%, only Troc generated 15% of the correct product.

Synthesis of BocAsp(Mop)OH

BocAspO$^t$Bu (1.38 mmoles) was dissolved in Ethanol/$H_2O$ (9:1), and this solution was titrated with a solution of CsOH 20% to pH 7.0 and dried under vacuum. The solid was washed with THF and dried under vacuum to eliminate excess water and finally freeze dried. The resulting oil was diluted with 4 ml of dry DMF and reacted with α-bromopropiophenone (1.3 mmoles) overnight at room temperature. The mixture was filtered to eliminate a white precipitate, and the DMF solution was dried under vacuum. The resulting oil was diluted with ethyl acetate, and the organic phase was washed with 1M $NaHCO_3$ (4 times), washed with saturated NaCl, dried with $MgSO_4$, and the organic phase evaporated under vacuum and freeze dried.

The resulting BocAsp(OMop)O$^t$Bu (single spot by TLC, $R_f$ 0.95 chloroform:methanol:acetic acid 90:8:2) was deprotected using TFA:TIS:$H_2O$ (95:2.5:2.5 V/V) for 1.5 hour. TFA was evaporated under vacuum and remaining TFA eliminated by several cycles of acetonitrile evaporation. The resulting oil was solubilized in 6 ml of ethanol:water (1:1), $Boc_2O$ was added (2 mmoles) and the pH adjusted and maintained at 9 with addition of NaOH during 1 hour. The solution was concentrated under vacuum and extracted with ethyl acetate after acidification with $KHSO_4$ to pH 3.5. The pooled organic fractions were washed with saturated NaCl, dried with $MgSO_4$ and finally concentrated. The oily product was used without further purification for coupling to MPAL resin using PyBop as the activator.

Zn/Acetic Acid Mop Removal

The purified peptide LYRAD(Mop)CSYRFL (SEQ ID NO: 3) obtained via ligation, was solubilized in aqueous 30% acetic acid, the solution was mixed with activated zinc powder for 30 minutes. The solution was recovered and the final product obtained by a desalting step with no further purification. Zinc powder (1 g) had previously been acid washed, as follow: 1N aqueous HCl (4×4 ml, 3 minute), $H_2O$ (4×4 ml, 1 minute), and kept in $H_2O$ until used (prepared daily).

Ligation with Asp/Glu Unprotected Side Chains

To investigate ligation at the Asp/Cys or Glu/Cys sites, Boc chemistry was used to synthesize two test peptide C-terminal thioesters, (1) LYRAD-thioester (SEQ ID NO: 4), and (2) LYRAE-thioester (SEQ ID NO: 5), wherein the side chain carboxy protecting group for Asp and Glu is cyclohexyl ester, and a free carboxyl peptide (3) CSYRFL (SEQ ID NO: 6). These short peptides were selected to increase the probability to detect by HPLC presence of side reactions. After HF cleavage, the thioester products presented a good HPLC analytical profile, with only one major component present for each peptide, confirming the stability of these specific thioesters in acidic conditions. When aspartyl thioester peptide 1 was used to conduct a ligation reaction with the C-terminal peptide 2, with standard native chemical ligation conditions (pH 6.5, 1% thiophenol and 1% benzyl mercaptan) after 2 hours, the presence of two ligated products was noticed with slightly different retention times ($R_f$), both presenting the expected mass for the correct product. The relative ratio of the two products was 1:2, with the more hydrophobic product in excess. The same result was obtained when the ligation was conducted with the C-terminal Glutamyl thioester peptide, although with a smaller quantity of the more hydrophilic product, with a relative ratio of 1:4. The same result was obtained when the reaction was conducted at pH 6.2 and at pH 7.0. Elimination of the benzyl mercaptan and use of only 0.1% of thiophenol did not modify the results for both peptides. To correctly define the nature of the impurities, the native sequences (4) LYRADCSYRFL (SEQ ID NO: 7), (5) LYRAECSYRFL (SEQ ID NO: 8) were completely synthesized by solid phase techniques, as well as the unnatural isomers (6) LYRAD(β)CSYUFL (SEQ ID NO: 9) and (7) LYRAE(γ)CSYRFL (SEQ ID NO: 10). Comparing the $R_f$ of these products with the ligation products it was confirmed that, both for the Asp ligation and for the Glu ligation, the two more hydrophilic compounds corresponded to the unnatural backbone isomers providing evidence that atoms of the thioester rearrange and migrate to the side chain carboxyl. Further evidence was provided from digestion with the enzyme SV8-protease. This proteolytic enzyme, selective for Asp-Xaa and Glu-Xaa, readily digested both the Glu and Asp ligation products that were more hydrophobic, but was not effective with the two impurities. The same results were obtained with the fully synthetic products, with product 6 and 7 being unaffected by the enzyme.

Selection of Side Chain Protection for Glutamyl Thioesters.

To avoid this undesired side reaction, preferably a protecting group is selected for the side-chain carboxy that has the following characteristic: (i) stable to HF cleavage; (ii) stable during the ligation reaction; and (iii) easily removed after the ligation reaction, preferably under conditions that will not jeopardize the integrity of a fully deprotected protein. Most of the available protecting groups will not withstand the first requirement. The following protecting groups were selected for this experiment: 9-fluorenylmethyl ester (OFm)[al-Obeidi, F., et al. *Int J Pept Protein Res* 1990;35(3):215-8] and (phenylsulfonyl)ethyl ester (OPse)[Lee, Y. S., et al. *J Pept Res* October 1999;54(4):328-35]. Solid phase synthesis of (8) LYRAE(OFm)-thioester (SEQ ID NO: 11) and (9) LYRAE(OPse)-thioester (SEQ ID NO: 12) resulted in the correct peptides in both cases, with the OPse group somewhat superior in this experiment. The OFm group was associated with the presence of multiple impurities, specifically loss of OFm group (~20% of the crude material) [Xue, C. B., et al. *Int J Pept Protein Res* 1991;37(6):476-86] and the alkylation of the OFm group by Br-Z (~25% of the crude material). This problem is limited to peptides containing a tyrosine, but this side reaction has also been reported in the case of the Bzl protecting group [Robles, J., et al. Int. *J. Pept. Protein Res.* 1994; 43(4): 359-62]. A further disadvantage of the OFm group lies in its high hydrophobicity, resulting in a particularly high $R_f$, a characteristic potentially problematic for peptide solubility when applied to a large peptide fragment.

When these peptides were tested in a native chemical ligation reaction, at pH 6.2, both peptides generated the expected protected products in two hours. This was expected since both Asp and Glu are reported to be a favorable site for a ligation reaction [Hackeng, T. M., et al. *Proc. Natl. Acad. Sci. USA.* 1999; 96 (18):10068-73]. Stability of these protecting groups was investigated by conducting the ligation at different pH and for different times (Table 1). The OPse group was less stable, with faster hydrolysis at higher pH. Preferred conditions include a minimal ligation time and a pH under 6.5. OFm was completely stable in the range of pH analysed.

TABLE 1

Conditions tested for OFm and OPse deprotection.

| Conditions | Results for Opse (% of deprotection/time) | Results for OFm (% of deprotection/time) |
|---|---|---|
| NaHCO₃ 0.2 M pH = 9 | 50.33%/two days | — |
| NaHCO₃ 0.2 M pH = 10 | 44.12%/two days | — |
| NaHCO₃ 0.2 M pH = 11 | 39.82%/two days | — |
| Na₂CO₃ 0.2 M pH = 12 | 38.57%/two days | — |
| NaHCO₃ 0.2 M, 10% BME, pH = 9 | 100%/2 hours | — |
| Na₂CO₃ 0.2 M, 10% BME, pH = 12 | 100%/2 hours | — |
| 20% pip., 20% DMF | — | 70%/2 hours |
| 20% pip., 20% DMF, 10% BME | — | 100%/15 min |
| 200 eq. DEA, 10% BME | — | 100%/2 hours |

Protecting group OPse is preferred in some aspects, because it can be directly removed in the ligation media, increasing the final recovery. A series of deprotection conditions were tested, using different pH and reagents (Table 1). OPse required less drastic, conditions; it was removed in 2 hours in 0.1M Na₂CO₃, 10% BME, pH10 at 37° C. OFm was removed in 15 minutes in presence of 10% BME, 20% DMF, 20% piperidine, pH12-13. β-mercaptoethanolarnine affected the rate of deprotection. When these conditions were applied on (12) LYRAE(OPse)CSYRFL (SEQ ID NO: 13) and (13) LYRAE(OFm)CSYRFL (SEQ ID NO: 14), in both cases only the correct backbone peptide was generated, with no side reactions.

Aspartic Acid Protection Removed By Reduction.

A class of protecting groups that are stable to HF but are promptly removed in acidic conditions are represented by either the Phenacyl esters (OPac) [Stalakatos, G. C., et al. *J. Chain. Soc.* 1966; 11918] or by the 2,2,2-trichloroethyl esters (Troc) [Woodward, R. B., at al. *J. Am. Chem Soc.* 1966; 88: 852]. The Asp derivatives of these groups were synthesized with a series of test peptides by a combination of Fmoc and Boc chemistry, with the aim to investigate the stability of these groups in the ligation conditions. Since there have been controversial reports on OPac stability [Yang, C. C., at al. *J. Am. Chem Soc.* 1976; 41: 1032-104110; Bodanszky, M., et al. *J. Org. Chem.* 1978; 43: 3071-3073] and with the aim of reducing potential hydrolysis, a sterically hindered version of Opac was designed by introducing an extra methyl in position 1:1-methyl-2-oxo-2-phenyl ester (OMop). On the other hand, two methoxy groups were introduced in positions 2' and 4' of the phenyl group to verify the incidence of the phenyl ring electron donating effect, generating the (2'-4'-dimethoxy)-phenacyl group (diMeOPac). The following compounds were synthesized: (14) Fmoc-D(Troc)YAKYAKL (SEQ ID NO: 15), (15) Ac-D(OPac)YAKYAKL (SEQ ID NO: 16) (16) Ac-D(OMop)YAKYAKL (SEQ ID NO: 171 and (17) Ac-D (diMeOPac)YAKYAKL (SEQ ID NO: 18). As reported in Table 2, the OMop group presented the higher stability, with a half-life in the ligation condition of 500 hours, sufficient to withstand a ligation. The diMeOPac presented higher stability compared to the OPac group, but less then half of the half-life of OMop. And Troc provided a half-life of less than 2 hours.

TABLE 2

Stability of the different Asp protection at pH 6.5, 1% thiophenol.

| Protection | Hydrolysis $t_{1/2}$ (Hours) |
|---|---|
| OPac | 1.2 |
| Troc | 1.5 |
| OdiMeOPac | 3.8 |
| OMop | 9.9 |

Test of Ligation with Asp(Mop) Thioester.

BocAsp(Mop) was readily synthesized with only slight modifications on existing procedure for BocAsp(Pac) (Yang et al. *J. Am. Chem. Soc.* 41: 1032 (1976)). Briefly α-bromopropiophenone was reacted with the cesium salt of BocAsp-ᵗBu, both Boc and the t-Butyl ester were removed in one step with TEA, and the amine protected with Boc. No attempt was made to resolve the two diastereoisomers, since the protecting group is eliminated at the end of the ligation reaction. The synthesis of LYRAD(Mop)-sr (SEQ ID NO: 19) did not evidence any problem, and the final peptide was recovered in theoretical yield. At this level, it was not possible to detect the two different diastereoisomers derived from the Mop protection. Ligation with CSYRFL (SEQ ID NO: 6) was completed in 4 hours at pH 6.5, with generation of a unique ligated product, still possessing the Mop protection. The final product LYRAD(●)CSYRFL (SEQ ID NO: 20) was obtained by treatment of purified LYRAD(OMop)CSYRFL (SEQ ID NO: 21) with Zn/Acetic Acid for 30 minutes, confirming that introduction of the methyl did not affect the rate of reduction.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A method of chemically ligating two oligopeptides, wherein a first oligopeptide thioester having an acidic C-terminal amino acid, said acidic C-terminal amino acid having a thioester moiety, a side chain, and a side chain protecting group selected from the group consisting of: 9-fluorenylmethyl ester, (phenylsulfonyl)ethyl ester, 2,2,2-trichloroethyl ester, and a phenacyl ester, such that said side chain protecting group substantially prevents rearrangements between atoms of said side chain and atoms of said thioester moiety, is contacted with a second oligopeptide having an N-terminal amino acid under chemical ligation conditions such that said thioester moiety of said first oligopeptide thioester ligates to said N-terminus of said second oligopeptide to form an oligopeptide or polypeptide product.

2. The method of claim 1 wherein said side chain protecting group is a phenacyl ester having the formula:

wherein $R^{13}$ and $R^{14}$ are each electron-donating groups.

3. The method of claim 2 wherein $R^{13}$ and $R^{14}$ are each alkyl having from 1 to 3 carbon atoms.

4. The method of claim 3 wherein $R^{13}$ is methyl or ethyl.

5. The method of claim 1 wherein said N-terminal amino acid of said second oligopeptide is cysteine or an amino acid with a removable ethylthiol moiety.

6. The method of claim 1 wherein one of said first and second oligopeptide is attached to a solid support.

* * * * *